United States Patent [19]

Burns et al.

[11] Patent Number: 5,454,789
[45] Date of Patent: Oct. 3, 1995

[54] INNERLESS DILATATION BALLOON CATHETER

[75] Inventors: Matthew M. Burns, Orono; David W. Lodin, Maple Grove, both of Minn.

[73] Assignee: SciMed Life Systems, Inc., Minneapolis, Minn.

[21] Appl. No.: 313,533

[22] Filed: Sep. 27, 1994

Related U.S. Application Data

[63] Continuation of Ser. No. 185,311, Jan. 21, 1994, abandoned, which is a continuation of Ser. No. 79,151, Jun. 17, 1993, abandoned, which is a continuation of Ser. No. 748,255, Aug. 21, 1991, Pat. No. 5,221,260, which is a continuation-in-part of Ser. No. 596,573, Oct. 11, 1990, Pat. No. 5,085,636, which is a continuation of Ser. No. 297,078, Jan. 13, 1989, abandoned, said Ser. No. 748,255, is a continuation-in-part of Ser. No. 730,224, Jul. 15, 1991, abandoned, which is a continuation of Ser. No. 337,272, Apr. 13, 1989, Pat. No. 5,032,113.

[51] Int. Cl.[6] .................................................. A61M 29/02
[52] U.S. Cl. .......................................... 604/99; 606/194
[58] Field of Search .............................. 604/96–103, 264, 604/280, 282; 606/192–196; 600/18

[56] References Cited

U.S. PATENT DOCUMENTS

| | | |
|---|---|---|
| 3,402,717 | 9/1968 | Doherty . |
| 3,675,658 | 7/1972 | Taylor . |
| 3,707,151 | 12/1972 | Jackson . |
| 3,726,283 | 4/1973 | Dye et al. . |
| 4,085,757 | 4/1978 | Pevsner . |
| 4,102,342 | 7/1978 | Akiyama et al. . |
| 4,213,461 | 7/1980 | Pevsner . |
| 4,240,411 | 12/1980 | Hosono ........................ 128/4 |
| 4,276,874 | 7/1981 | Wolvek et al. . |
| 4,281,660 | 8/1981 | Fujiwara ...................... 128/642 |
| 4,285,341 | 8/1981 | Pollack . |
| 4,413,989 | 11/1983 | Schjeldahl et al. .......... 604/96 |
| 4,456,000 | 6/1984 | Schjeldahl et al. .......... 606/194 X |
| 4,509,523 | 4/1985 | Pevsner ....................... 128/658 |
| 4,545,367 | 10/1985 | Tucci . |
| 4,598,707 | 7/1986 | Agdanowski et al. ....... 128/207.15 |
| 4,606,347 | 8/1986 | Fogarty et al. ............... 606/194 |
| 4,616,653 | 10/1986 | Samson et al. . |
| 4,638,805 | 1/1987 | Powell . |
| 4,646,742 | 3/1987 | Packard et al. . |
| 4,665,925 | 5/1987 | Millar .......................... 128/663 |
| 4,684,363 | 8/1987 | Ari et al. ..................... 604/98 |
| 4,715,378 | 12/1987 | Pope, Jr. et al. . |
| 4,762,129 | 8/1988 | Bonzel . |
| B1 4,762,129 | 7/1991 | Bonzel ......................... 606/194 |
| 4,782,834 | 11/1988 | Maguire et al. . |
| 4,793,350 | 12/1988 | Mar et al. . |
| 4,811,737 | 3/1989 | Rydell . |
| 4,813,934 | 3/1989 | Engelson et al. ............ 604/99 |
| 4,819,630 | 4/1989 | DeHart . |
| 4,819,637 | 4/1989 | Dormandy, Jr. et al. . |

(List continued on next page.)

FOREIGN PATENT DOCUMENTS 0371486  11/1988  European Pat. Off. .

*Primary Examiner*—Corrine Maglione
*Assistant Examiner*—Adam J. Cermak
*Attorney, Agent, or Firm*—Nawrocki, Rooney & Sivertson

[57] ABSTRACT

An "innerless" balloon catheter controls fluid flow past the guide wire at the distal end of the catheter by a combination of flow resistance and a pressure responsive valve. The catheter includes a shaft which carries an inflatable balloon at its distal end. The shaft has a lumen therethrough with the lumen being in fluid communication with the balloon interior for inflating and deflating the balloon via the shaft lumen. The catheter further includes a lumen extension through the balloon, with the lumen extension being in fluid communication with the shaft lumen. A guide wire extends through the shaft lumen and the lumen extension and out the distal end of the balloon. The resistance to fluid flow past the guide wire in the lumen extension is substantially greater than the resistance to fluid flow between the shaft lumen and the balloon interior. A valve member is responsive to the pressure in the balloon interior for blocking fluid flow through the lumen extension during continuing inflation and at least the initial deflation of the balloon.

10 Claims, 2 Drawing Sheets

U.S. PATENT DOCUMENTS

| | | | |
|---|---|---|---|
| 4,820,262 | 4/1989 | Finney | 604/8 |
| 4,820,349 | 4/1989 | Saab . | |
| 4,846,174 | 7/1989 | Willard et al. . | |
| 4,848,344 | 7/1989 | Sos et al. . | |
| 4,877,031 | 10/1989 | Conway et al. . | |
| 4,906,241 | 3/1990 | Noddin et al. | 606/194 |
| 4,917,666 | 4/1990 | Solar et al. | 604/95 |
| 4,932,959 | 6/1990 | Horzewski et al. | 606/194 |
| 4,944,745 | 7/1990 | Sogard et al. | 606/194 |
| 4,955,895 | 9/1990 | Sugiyama et al. | 606/194 |
| 4,976,720 | 12/1990 | Machold et al. | 606/194 |
| 5,002,532 | 3/1991 | Gaiser et al. | 604/101 |
| 5,032,113 | 7/1991 | Burns | 604/96 |
| 5,035,705 | 7/1991 | Burns | 606/194 |
| 5,047,045 | 9/1991 | Arney et al. | 606/194 |
| 5,059,176 | 10/1991 | Winters | 604/96 |
| 5,061,273 | 10/1991 | Yock | 606/194 |
| 5,078,727 | 1/1992 | Hannam et al. | 606/194 |
| 5,085,636 | 2/1992 | Burns | 604/99 |
| 5,100,385 | 3/1992 | Bromander | 604/99 |
| 5,102,390 | 4/1992 | Crittenden et al. | 604/96 |
| 5,135,487 | 8/1992 | Morrill et al. | 604/96 |
| 5,171,222 | 12/1992 | Euteneuer et al. | 604/102 |
| 5,176,637 | 1/1993 | Sagae | 604/96 |
| 5,178,608 | 1/1993 | Winters | 604/99 |
| 5,221,260 | 6/1993 | Burns et al. | 604/99 |

INNERLESS DILATATION BALLOON CATHETER

This is a continuation of application Ser. No. 08/185,311, filed Jan. 21, 1994, (abandoned) which is a continuation of Ser. No. 08/079,151 filed on Jun. 17, 1993, (abandoned) which is a continuation of Ser. No. 07/748,255, filed Aug. 21, 1991, now U.S. Pat. No. 5,221,260, which is a continuation-in-part of Ser. No. 07/596,573, filed Oct. 11, 1990, now U.S. Pat. No. 5,085,636, which is a continuation of Ser. No. 07/297,078, filed Jan. 13, 1989, (abandoned) said 07/748,255 is also a continuation-in-part of Ser. No. 07/730,224, filed Jul. 15, 1991, (abandoned) which is a continuation of Ser. No. 07/337,272, filed Apr. 13, 1989, now U.S. Pat. No. 5,032,113.

BACKGROUND OF THE INVENTION

The present invention relates to angioplasty and, in particular, to a dilatation balloon catheter.

Angioplasty has gained wide acceptance in recent years as an efficient and effective method for treating types of vascular diseases. In particular, angioplasty is widely used for opening stenoses in the coronary arteries. It is also used for treatment of stenoses in other parts of the vascular system.

A common form of angioplasty makes use of a dilatation catheter which has an inflatable balloon at its distal end. With the aid of fluoroscopy, a physician guides the catheter through the vascular system until the balloon is positioned across the stenosis. The balloon is then inflated by supplying fluid pressure through an inflation lumen to the balloon. Inflation of the balloon causes stretching of the artery and a pressing of the lesion into the artery wall to reestablish acceptable blood flow through the artery.

It is apparent that treatment with a dilatation catheter requires that the catheter reach and cross a stenosis. In order to extend treatment to very tight stenosis with small openings, there has been a continuing effort to reduce the profile (and shaft diameter) of the catheter. In addition, a successful dilatation catheter must be sufficiently flexible to pass through tight curvatures through the very tortuous path of the vascular system.

A further requirement of a successful dilatation catheter is its "pushability." This involves a transmission of longitudinal force along the catheter from its proximal end to its distal end so that a physician can push the catheter through the vascular system and the stenosis.

It is a common practice to employ a guide wire to establish the path to the stenosis. The dilatation catheter is then fed over the guide wire until the balloon is positioned within the stenosis. As an alternative, the catheter can serve as its own guide wire. One disadvantage to the self-guiding approach is that there is nothing to maintain the desired position within the vascular system when replacing the catheter— as when a larger or smaller balloon is desired, for example. Such replacement requires that the path to the stenosis must be reestablished when the catheter is replaced.

The use of a catheter assembly employing a guide wire provides the advantage of maintaining a path to the stenosis during a catheter exchange. One problem with many so-called "over-the-wire" catheters is the need to accommodate the guide wire within the catheter which has often been accomplished through the provision of a separate guide wire lumen. This has resulted in a larger profile (and shaft) to allow for the separate guide wire lumen.

SUMMARY OF THE INVENTION

The present invention is an "innerless" balloon catheter which uses a combination of resistance to fluid flow past a guide wire and a fluid pressure responsive valve to control fluid flow during inflation and deflation of the balloon. The catheter includes a shaft which carries an inflatable balloon at its distal end. The shaft has a lumen which is in fluid communication with the balloon interior. The shaft lumen also accommodates the guide wire without a provision for a separate guide wire lumen through at least a substantial portion of the catheter shaft.

In accordance with the present invention, a lumen extension extends through the balloon, with the lumen extension being in fluid communication with the shaft lumen. A guide wire extends through the shaft lumen and the lumen extension and out the distal end of the balloon. The resistance to fluid flow past the guide wire in the lumen extension is substantially greater than the resistance to fluid flow between the shaft lumen and the balloon interior. A valve responds to the pressure in the balloon interior for blocking fluid flow through the lumen extension during continuing inflation of the balloon and at least the initial deflation of the balloon interior. In a preferred embodiment, the valve is formed as a resilient member within the lumen extension, and surrounds the guide wire within the lumen extension to engage the guide wire when the balloon interior is pressurized.

DETAILED DESCRIPTION OF THE PREFERRED EMBODIMENTS

An over-the-wire dilatation catheter necessarily requires a passage for the guide wire with an opening of the passage at the distal end of the catheter having a potential for fluid communication between the patient's body and catheter lumen. When the guide wire extends through a dedicated guide wire lumen which is not pressurized or depressurized during inflation and deflation of the balloon, this guide wire opening poses little difficulty. However, in an "innerless" catheter in which the guide wire extends through the same lumen which is used for inflation/deflation of the balloon, a control of fluid flow between the catheter and the patient's body is at least desirable, if not necessary in order to achieve reliable inflation and deflation of the balloon. The present invention provides this control through the use of a lumen extension which passes through the balloon and which controls fluid flow by the combined effects of a resistance to fluid flow resulting from a desired cooperation between the guide wire and lumen extension and the action of a valve member responsive to fluid pressure in the balloon interior. The valve member is active during continuing inflation of the balloon as well as during at least the initial deflation of the balloon.

Figure 1:
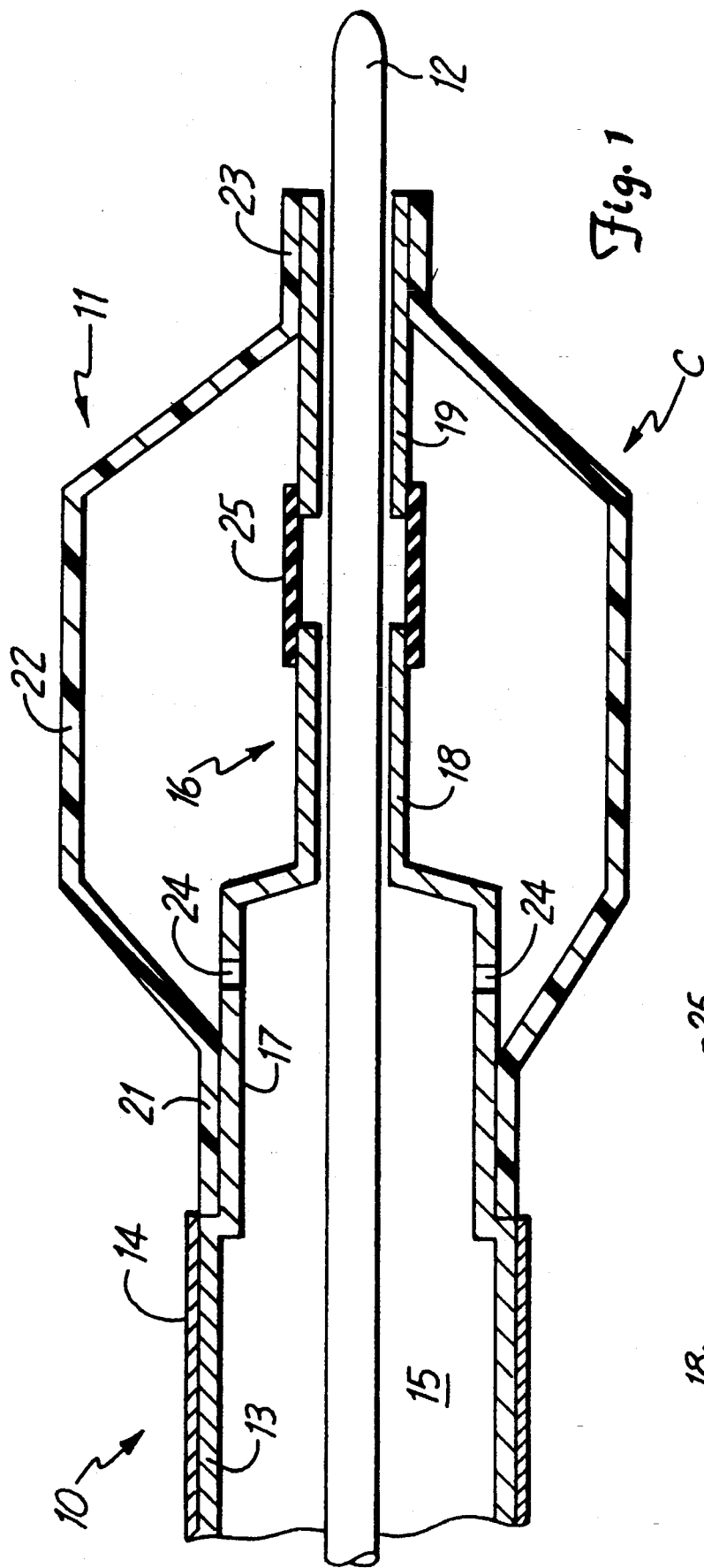
FIG. 1 is a partial sectional view of a preferred embodiment of a portion of a balloon catheter assembly in accordance with the present invention.

FIG. 1 is a sectional view showing the distal end of a balloon catheter C in accordance with the present invention. Catheter C includes catheter shaft 10 and balloon 11, and is used in conjunction with guide wire 12. Shaft 10 is formed of an elongated flexible tube 13, preferably a stainless steel or polyamide with a low friction coating 14 such as PARALENE (poyl p-xylene) or TEFLON (PTFE fluorocarbon). Depending on the characteristics desired, shaft 10 can be of an integral or multi-part construction. In one embodiment, shaft 10 has an inside diameter of about 0.027 inch and outside diameter of about 0.031 inch, and a shaft coating 14 thickness of about 0.0008 inch. Shaft 10 is mounted at its proximal end to an inflation device (not shown) which provides fluid under pressure to lumen 15 of shaft 10 for balloon inflation. Lumen 15 serves as a passage for fluid as well as for guide wire 12.

Lumen extension 16 extends from the distal end of shaft 10. Lumen extension 16 includes a proximal portion formed by shoulder section 17 and intermediate section 18 and a distal portion formed by stub section 19. Each section is generally cylindrical, with sections 18 and 19 being of a diameter less than that of shoulder section 17. As can be seen in FIG. 1, lumen extension 16 extends through balloon 11.

Balloon 11, which is preferably a polymer material such as polyolefin, has a proximal or waist segment 21, a distensible balloon segment 22 and a small diameter distal segment 23. Waist segment 21 is bonded to shoulder section 17 of the lumen extension, while distal segment 23 of balloon 11 is bonded to the stub section 19. Perforations 24 through shoulder section 17 of lumen extension 16 provide ports for inflation/deflation of balloon 11 by control of the pressure in shaft lumen 15.

Shoulder section 17 and intermediate section 18 of lumen extension 16 are shown integrally formed with tube 13 of shaft 10. Alternatively, those sections may be separately formed of a suitable material with appropriate securement to achieve the relationships indicated in FIG. 1.

Intermediate section 18 and distal section 19 of lumen extension 16 are shown spaced from each other to form a "break" within lumen extension 16. Sections 18 and 19 of lumen extension 16 are generally cylindrical with the break extending around the entirety of the periphery of lumen extension 16. Valve member 25 spans the break in lumen extension 16 and is suitably secured to lumen extension 16 such that the break is sealed and the integrity of the balloon interior is maintained. Valve member 25 is preferably made of a flexible polymeric material such that inflation/pressurization of balloon 11 causes a deflection of valve member 25 into and through the break in lumen extension 16 and into engagement with guide wire 12 as will be described further with respect to FIG. 2.

As is typical of over-the-wire catheters, guide wire 12 extends through shaft 10 and balloon 11 and out the distal end of catheter C. The opening in the balloon 11 through which guide wire 12 extends provides an opening for fluid flow through lumen extension 16 between shaft lumen 15 and the exterior of catheter C. In the present invention, this fluid exchange is controlled, in part, by configuring lumen extension 16 and guide wire 12 such that the resistance to fluid flow through lumen extension 16 with guide wire 12 in place is significantly higher than the resistance to fluid flow between shaft lumen 15 and the interior of balloon 11, via perforations 24. Thus, when shaft lumen 15 is pressurized, balloon 11 will inflate. Similarly, the fluid within the interior of balloon 11 can be withdrawn via shaft lumen 15 to deflate balloon 11.

Figure 2:
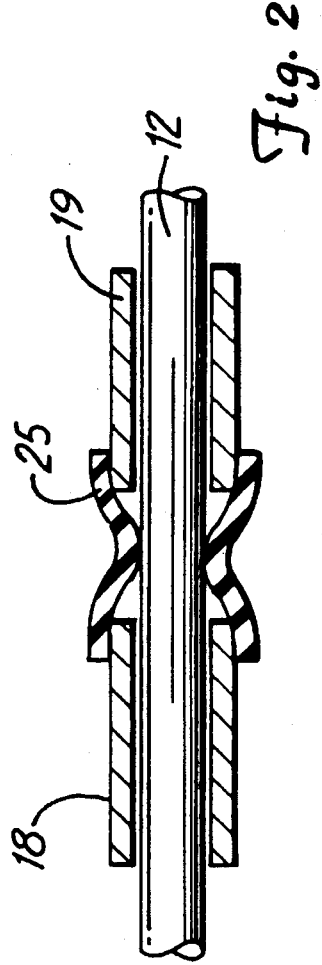
FIG. 2 is a partial sectional view showing in detail the cooperation between the valve member illustrated in FIG. 1 and the guide wire when the balloon interior is pressurized.

In accordance with the present invention, fluid flow through lumen extension 16 is further controlled via valve member 25, which responds to the pressure in the interior of balloon 11 causing it to converge toward guide wire 12 (through the break in the lumen extension 16 formed by sections 18 and 19) until valve member 25 engages the guide wire 12 as shown in FIG. 2. This positive control of fluid flow through lumen extension 16 is initiated when fluid pressure in the interior of balloon 11 reaches a threshold value and continues during continued inflation of the balloon. The positive control of fluid flow through the lumen extension 16 via valve member 25 will also be continued during at least the initial deflation of the interior of the balloon 11; that is, until the pressure within the interior of balloon 11 decreases below the threshold value and no longer acts sufficiently on valve member 25 to extend it into contact with guide wire 12. During contact between valve member 25 and guide wire 12, axial movement of catheter C relative to the guide wire 12 is restricted. On the other hand, when fluid pressure is not being applied, guide wire 12 and catheter C can move freely with respect to one another, while providing a tolerance fluid seal".

The particular flow characteristics necessary to accomplish the stated purposes are dependent on the size of perforations 24 and the relative sizes and deforming characteristics of the materials forming balloon 11, including valve member 25, but are within the abilities of one ordinarily skilled in the art given the design criteria stated herein and the teachings of the above-incorporated patent applications.

Figure 3:
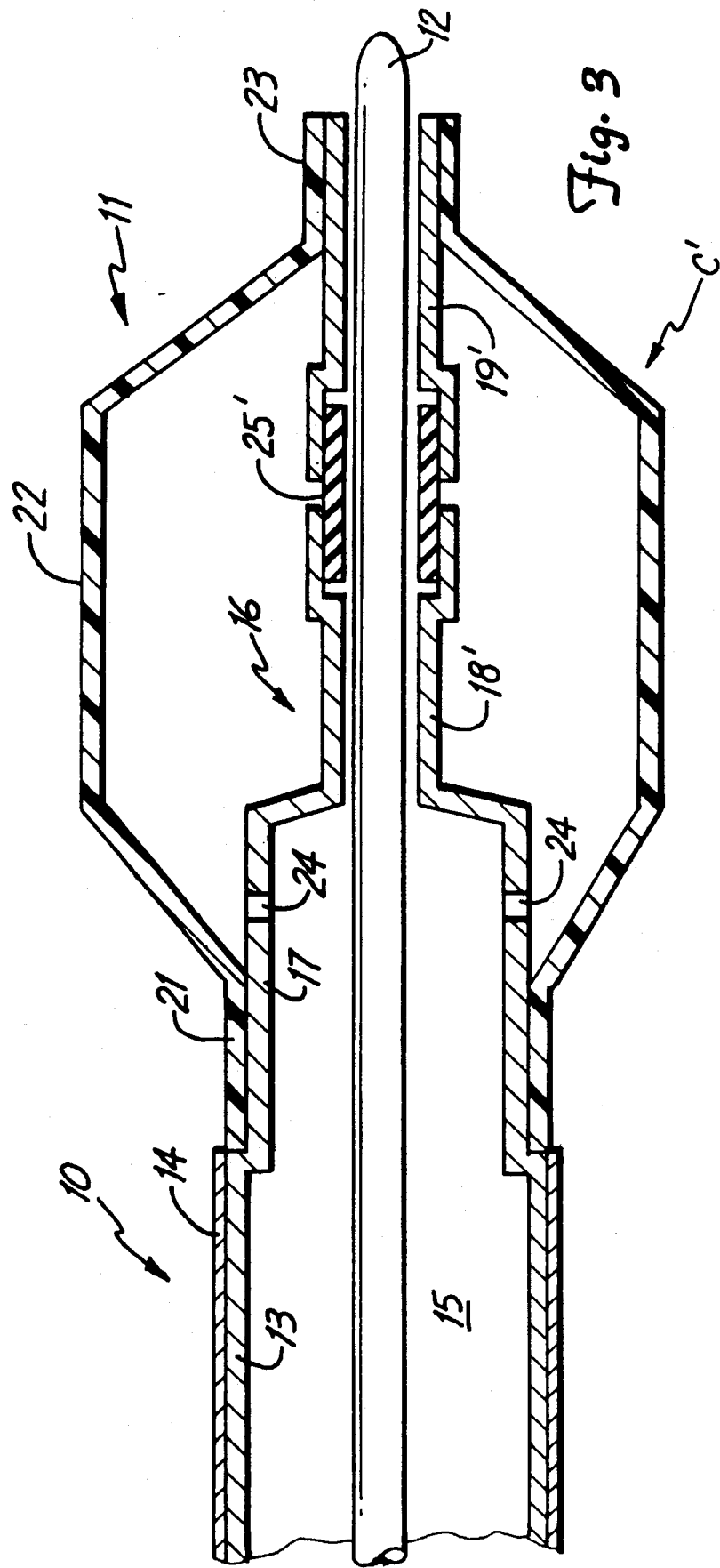
FIG. 3 is a partial sectional view of a further preferred embodiment of a portion of a balloon catheter assembly in accordance with the present invention.
Figure 4:
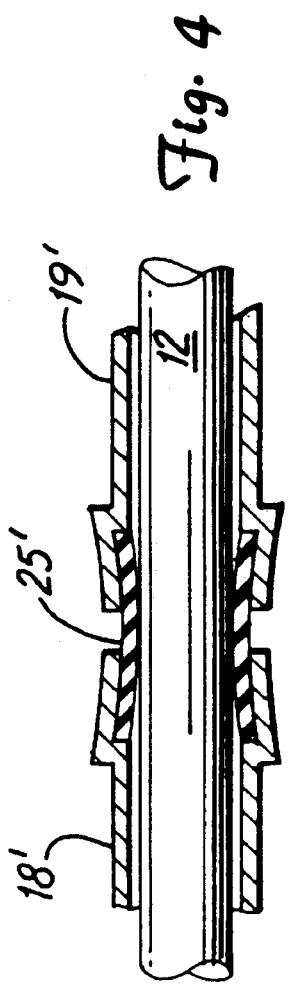
FIG. 4 is a partial sectional view showing in detail the cooperation between the valve member illustrated in FIG. 3 and the guide wire when the balloon interior is pressurized.

FIGS. 3 and 4 show an alternative embodiment to that illustrated in FIGS. 1 and 2. Throughout the figures, like elements are designated by identical reference numerals. The primary difference in catheter C' of FIGS. 3 and 4 to catheter C of FIGS. 1 and 2 is in the formation of the break in the lumen extension 16 and the manner in which valve member 25 spans that break. As shown in FIGS. 3 and 4, each of sections 18' and 19' are formed with opposing enlarged or cup-shaped portions which open toward each other and whose termini define the break in lumen extension 16. That break is spanned by valve member 25' which is similar in construction to the valve member 25 of FIGS. 1 and 2 but which is smaller in diameter, the diameter of valve member 25' corresponding to the diameter of the main body of sections 18' and 19'. Valve member 25' is supported so that it is nonetheless responsive to pressure within the interior of balloon 11 such that pressure within balloon 11 causes valve member 25' to compress and engage guide wire 12 as illustrated in FIG. 4. In the embodiment of FIGS. 3 and 4, flow restriction through lumen extension 16 is established on placement of the guide wire 12 with valve member 25' being active during continuing inflation and at least the initial deflation of the interior of balloon 11, as described above with reference to FIGS. 1 and 2.

Many modifications and variations of the present invention are possible in light of the above teachings. That is, the present invention provides a control of fluid flow from and to an over-the-wire catheter through the combined effects of a flow restriction established by the positioning of the guide wire through the catheter, and by an active valve element responsive to pressure within the balloon interior to act on the guide wire. Pressure responsive vale elements other than those specifically shown can be easily accommodated within the present invention. Further, the drawings are for purposes of illustration only and are not necessarily drawn to scale. It is therefore to be understood that, within the scope of the appended claims, the invention may be practiced otherwise than as specifically described.

What is claimed is:

1. In a catheter of the type having a shaft with at least one lumen extending from a proximal end to a distal end thereof and having a balloon mounted proximal said distal end with means for fluid communication between said at least one lumen and the interior of said balloon, the improvement comprising:

a. a guide wire received by said lumen; and
   b. a combination of means including means for passive flow resistance, said passive show resistance means including a portion of said lumen distal of said means for fluid communication having an inner diameter relative to the outside diameter of said guide wire which permits free relative movement of said guide wire due to a gap therebetween and said catheter while providing a resistance to fluid flow past said guide wire in said portion of said lumen, said passive flow resistance means providing a tolerance fluid seal in the absence of fluid pressure in the interior of the balloon, and including valve means responsive to pressure in the interior of the balloon for reducing fluid flow through said lumen at a location that corresponds to said valve means; said location being distal to said means for fluid communication.

2. The catheter of claim 1 wherein said valve means comprises a flexible tube positioned within the interior of the balloon which has an outer surface exposed to fluid pressure within the interior of the balloon, the flexible tube having an inner surface which engages the guide wire to reduce fluid flow through the lumen extension when pressure on the outer surface is greater than on the inner surface.

3. The catheter of claim 2 wherein said means for passive flow resistance further includes a proximal portion connected to the shaft and a distal portion connected to a distal end of the balloon.

4. The catheter of claim 3 wherein the flexible tube extends between the proximal portion and the distal portion.

5. The catheter of claim 4 wherein the proximal portion has a first pocket at a distal end and the distal portion has a second pocket at a proximal end, and wherein the flexible tube has a first end positioned in the first pocket and a second end positioned in the second pocket.

6. A balloon catheter assembly comprising:

a. a shaft having a proximal end, a distal end, and a lumen which extends between the proximal end and the distal end;
   b. a balloon carried at the distal end of the shaft and means for fluid communication between the interior of said balloon and the lumen to permit inflation and deflation of the balloon;
   c. a guide wire;
   d. a portion of the lumen distal of said means for fluid communication having an inner diameter which permits free relative movement of the guide wire and the balloon catheter due to a gap therebetween and which provides a resistance to fluid flow past the guide wire in said portion of said lumen which is greater than resistance to fluid flow between the lumen and the interior of the balloon during at least a part of the inflation of the balloon; and
   e. valve means positioned within the interior of the balloon and extending circumferencially around the lumen at a location distal of said means for fluid communication; said valve means being responsive to pressure in the interior of the balloon for reducing fluid flow through the lumen distal of said means for fluid communication during at least a part of inflation of the balloon.

7. The balloon catheter assembly of claim 6 wherein the valve means comprises a flexible tube positioned within the interior of the balloon which has an outer surface exposed to fluid pressure within the interior of the balloon, the flexible tube having an inner surface which engages the guide wire to reduce fluid flow through the lumen distal of said means for fluid communication when pressure on the outer surface is greater than on the inner surface.

8. The balloon catheter assembly of claim 7 wherein the portion of the lumen having an inner diameter which permits free relative movement includes a proximal portion connected to the shaft and a distal portion connected to a distal end of the balloon.

9. The balloon catheter assembly of claim 8 wherein the flexible tube extends between the proximal portion and the distal portion.

10. The balloon catheter assembly of claim 9 wherein the proximal portion has a first pocket at a distal end and the distal portion has a second pocket at a proximal end, and wherein the flexible tube has a first end positioned in the first pocket and a second end positioned in the second pocket.

* * * * *

UNITED STATES PATENT AND TRADEMARK OFFICE
CERTIFICATE OF CORRECTION

PATENT NO.   :   5,454,789
DATED        :   Oct. 3, 1995
INVENTOR(S)  :   Burns et al.

It is certified that error appears in the above-identified patent and that said Letters Patent is hereby corrected as shown below:

Column 2, line 22, delete "lumenextension" and insert --lumen extension--.

Column 4, line 24, delete "seal"", and insert --seal--.

Column 4, line 64, delete "vale" and insert --valve--.

Column 5, line 13, delete "show" and insert --flow--.

Signed and Sealed this

Ninth Day of January, 1996

*Attest:*

BRUCE LEHMAN

*Attesting Officer*   *Commissioner of Patents and Trademarks*